(12) United States Patent
Piron et al.

(10) Patent No.: US 10,082,547 B2
(45) Date of Patent: Sep. 25, 2018

(54) OPERATION OF THE MAGNET OF A MAGNETIC RESONANCE IMAGING (MRI) SYSTEM

(71) Applicant: SYNAPTIVE MEDICAL (BARBADOS) INC., Bridgetown (BB)

(72) Inventors: Cameron Anthony Piron, Toronto (CA); Chad Tyler Harris, Toronto (CA); Jeff Alan Stainsby, Toronto (CA); Alexander Gyles Panther, Toronto (CA); Gal Sela, Toronto (CA)

(73) Assignee: Synaptive Medical (Barbados) Inc., Bridgetown (BB)

( * ) Notice: Subject to any disclaimer, the term of this patent is extended or adjusted under 35 U.S.C. 154(b) by 0 days.

(21) Appl. No.: 15/556,467

(22) PCT Filed: Mar. 11, 2015

(86) PCT No.: PCT/IB2015/051775
§ 371 (c)(1),
(2) Date: Sep. 7, 2017

(87) PCT Pub. No.: WO2016/142747
PCT Pub. Date: Sep. 15, 2016

(65) Prior Publication Data
US 2018/0052210 A1 Feb. 22, 2018

(51) Int. Cl.
*G01V 3/00* (2006.01)
*G01R 33/28* (2006.01)
*A61B 5/00* (2006.01)

(52) U.S. Cl.
CPC .......... *G01R 33/288* (2013.01); *A61B 5/0033* (2013.01); *A61B 2560/0266* (2013.01); *A61B 2562/0223* (2013.01)

(58) Field of Classification Search
CPC .......... G01R 33/288; A61B 2560/0266; A61B 5/0033; A61B 2562/0223
(Continued)

(56) References Cited

U.S. PATENT DOCUMENTS 3,549,860 A * 12/1970 Parker ................ G05D 23/1909
126/21 A
2007/0057786 A1 3/2007 McClure
(Continued)

FOREIGN PATENT DOCUMENTS

CA 2721794 A1 5/2012
JP 1-317630 A 11/1992
(Continued)

OTHER PUBLICATIONS

Authorized officer Blaine R. Copenheaver, PCT International Search Report/Written Opinion in PCT/IB2015/051775, dated Jul. 7, 2015, 17 pages.
(Continued)

*Primary Examiner* — Giovanni Astacio-Oquendo
(74) *Attorney, Agent, or Firm* — Fish & Richardson P.C.

(57) ABSTRACT

Some implementations provide a method for safe operation of a magnetic resonance imaging (MRI) system, the method including: determining, at least in part by using a sensor device, location information that indicates a location of an MR-incompatible object relative to the MRI system, the MRI system generating a polarizing magnetic field for imaging a subject; based on the determined location information, determining, by a control unit associated with the MRI system, that the MR-incompatible object poses an operational hazard to the MRI system; and in response to determining that the MR-incompatible object poses an operational hazard to the MRI system, reducing, by the control unit, a strength of the polarizing magnetic field.

7 Claims, 4 Drawing Sheets

(58) Field of Classification Search
USPC .............. 324/300, 263, 301; 250/221, 338.1
See application file for complete search history.

(56) References Cited

U.S. PATENT DOCUMENTS

| | | | |
|---|---|---|---|
| 2008/0281187 A1 | 11/2008 | Massengill | |
| 2009/0266887 A1 | 10/2009 | Molyneaux | |
| 2010/0137945 A1 | 6/2010 | Gadagkar | |
| 2010/0179763 A1 | 7/2010 | Overall | |
| 2010/0189328 A1 | 7/2010 | Boernert | |
| 2013/0314085 A1* | 11/2013 | Tokuda | G01R 33/546 324/309 |
| 2015/0145524 A1* | 5/2015 | Duncan | G01R 31/024 324/538 |
| 2016/0054370 A1* | 2/2016 | Fomin | G01R 31/025 324/509 |
| 2016/0178689 A1* | 6/2016 | Okita | G01R 31/024 324/509 |
| 2017/0042570 A1* | 2/2017 | Piron | A61B 17/3421 |

FOREIGN PATENT DOCUMENTS

| | | |
|---|---|---|
| JP | 2001-43468 A | 2/2001 |
| JP | 2005-192857 A | 7/2005 |
| JP | 2009-70259 A | 4/2009 |
| WO | WO2014129426 A1 | 8/2014 |

OTHER PUBLICATIONS

M. Klarhoefer et al., MRI-Compatible Optical Tracking Device with Active Markers, Proceedings of the International Society for Magnetic Resonance in Medicine (13) 2005, p. 2161.

International Search Report dated May 20, 2014 in corresponding International application No. PCT/JP2014/053662 (with English-language translation).

* cited by examiner

OPERATION OF THE MAGNET OF A MAGNETIC RESONANCE IMAGING (MRI) SYSTEM

BACKGROUND

The present disclosure relates to magnetic resonance imaging and, in particular, operation of the magnet of a magnetic resonance imaging (MRI) system.

SUMMARY

In one aspect, some implementations provide a method for safe operation of a magnetic resonance imaging (MRI) system, the method including: determining, at least in part by using a sensor device, location information that indicates a location of an MR-incompatible object relative to the MRI system, the MRI system generating a polarizing magnetic field for imaging a subject; based on the determined location information, determining, by a control unit associated with the MRI system, that the MR-incompatible object poses an operational hazard to the MRI system; and in response to determining that the MR-incompatible object poses an operational hazard to the MRI system, reducing a strength of the polarizing magnetic field.

Implementations may include one or more of the following features. The polarizing magnetic field may be substantially uniform. Determining that the MR-incompatible object poses an operational hazard to the MRI system may include determining that the MR-incompatible object is present within a safety zone of a main magnet of the MRI system. Determining that the MR-incompatible object poses an operational hazard to the MRI system may include determining that the MR-incompatible object is accelerating towards a main magnet of the MRI system. The sensor device comprises a camera and determining the location information may include performing image processing on images obtained from the camera to locate the MR-incompatible object relative to the MRI system. The sensor device may include one of: a Gauss meter, a Hall probe, a magnetic field probe, or an optical tracker. The sensor device may be mounted on the MR-incompatible object.

Determining the location information may include detecting a change in a current that powers a main magnet of the MRI system, the change being induced by a motion of the MR-incompatible object within the polarizing magnetic field. Reducing the strength of the polarizing magnetic field may include initiating a shutdown of a main magnet of the MRI system.

The method may further include ramping up the strength of the polarizing magnet field when the operational hazard to the MRI system posed by the MR-incompatible object no longer exists.

In another aspect, some implementations provide a magnetic resonance imaging (MRI) system, the MRI system including: a housing having a bore in which a subject to be imaged is placed; a main magnet accommodated by said housing and configured to generate a polarizing magnet field with the bore; pulse generating coils configured to generate and apply radio frequency (RF) pulses in sequence to scan the subject; gradient coils configured to provide perturbations to the polarizing magnet field that encode MRI signals acquired in response to the applied RF pulses; and a control unit coupled to the main magnet and configured to: access location information that indicates a location of an MR-incompatible object relative to the MRI system; based on the location information, determine whether the MR-incompatible object poses an operational hazard to the MRI system; and in response to determining that the MR-incompatible object poses an operational hazard to the MRI system, reduce a strength of the polarizing magnetic field.

Implementations may include one or more of the following features. The polarizing magnetic field may be substantially uniform. The control unit may be configured to receive location information of the MR-incompatible object from a sensor mounted on the MR-incompatible object. The sensor may include one of: a Gauss meter, a Hall probe, a magnetic field probe, or an optical tracker.

The MRI system may further include a camera, wherein the control unit is configured to process images from the camera to determine the location information of the MR-incompatible object.

The MRI system may further include a current sensor, wherein the control unit is configured to process a signal from the current sensor to detect a change in a current that powers the main magnet, the change being induced by a motion of the MR-incompatible object within the polarizing magnetic field.

To reduce the strength of the polarizing magnetic field, the control unit may be configured to initiate a shutdown of the main magnet.

BRIEF DESCRIPTION OF THE DRAWINGS

Embodiments will now be described, by way of example only, with reference to the drawings, in which.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

Magnetic resonance imaging (MRI) systems generally include a main magnet generating a magnetic field tens of thousands times stronger than the earth's magnetic field. As a result, in certain situations, the main magnet can attract MR-incompatible objects. For example, foreign metal objects, when brought within the vicinity of the magnetic field, can become projectiles flying into the main magnet and causing disastrous damage. In this example, MR-incompatible objects, such as an object including ferromagnetic material, can be attracted by the fringe field of the main magnet. The MR-incompatible objects can include carts, oxygen tanks, and tools (such as wrenches). Once attracted, these objects may be accelerated by the magnetic force imparted by the main magnetic field and can become high-velocity projectiles capable of damaging the magnet or harming a human patient. This is a significant operational hazard of the MRI system, especially when a patient is being scanned inside the magnet.

Some implementations of the present disclosure may include a detection mechanism for the MRI system to identify MR-incompatible objects within a safety zone of a magnet. The identification may classify the objects according to the corresponding operational hazards. If the MR-incompatible object is within a specific region (e.g., the fringe field of the system), then the MRI system may react by automatically initiating a protection sequence. In some instances, the MRI system may initiate an automatic winding down of the main magnetic field. For example, the MRI system may decrease the current through the superconducting wires to reduce the magnetic field or to completely shut off the field. In some instances where a patient is placed in the magnet's bore, the protection sequence may include deploying a protective physical barrier, such as airbag(s), to shield the patient from projectiles while the current (and thus magnetic field) is being shut down.

Figure 1A:
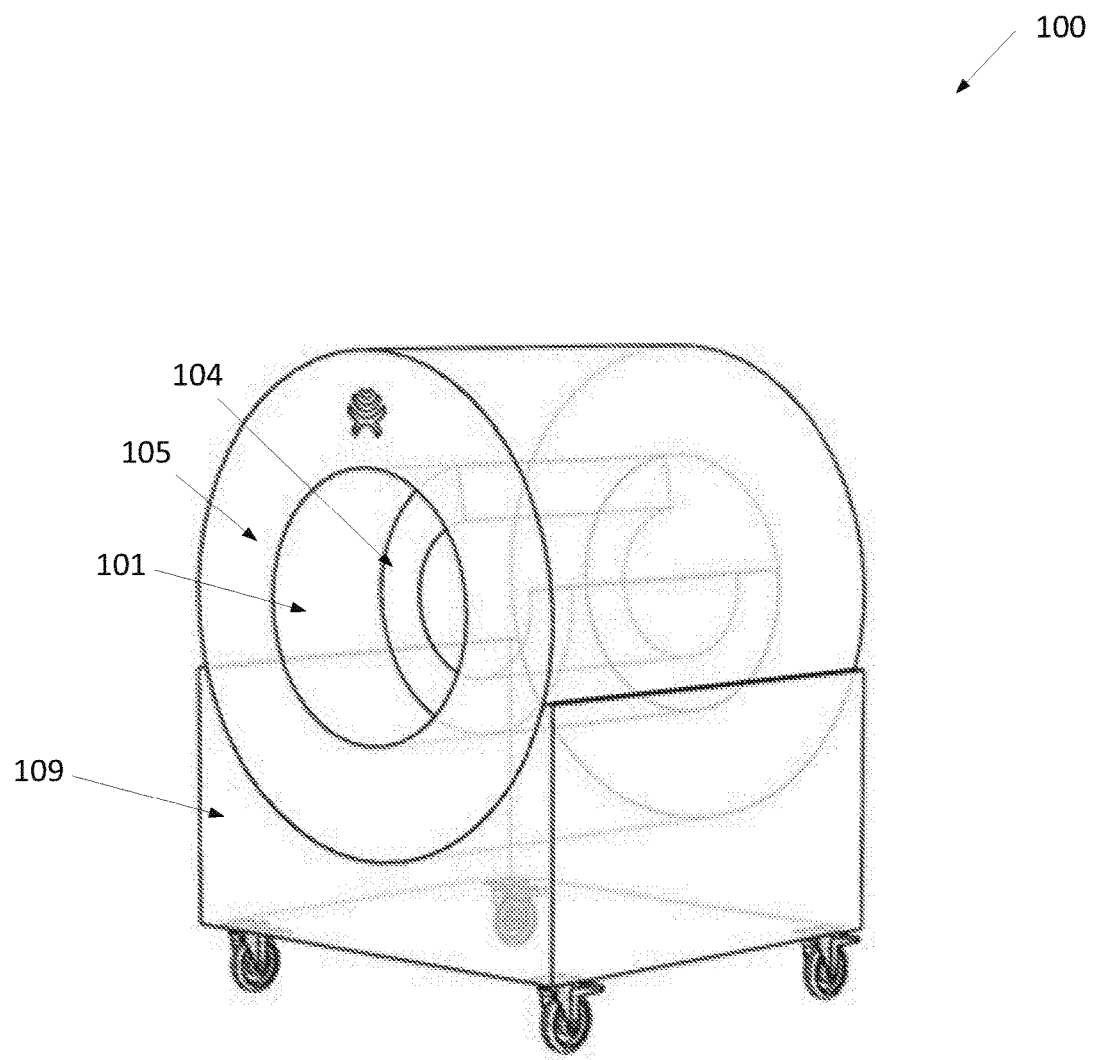
FIG. 1A shows a perspective view of an example of a magnetic resonance imaging (MRI) system configured for safe shutdown.

Referring now to FIG. 1A, an example of a magnetic resonance imaging (MRI) system 100 is shown in which a magnet housing 105 is placed on a base 109. Base 109 may include a portable cart, as shown. In some installations, base 109 may be affixed to the floor of the scanning room. Magnet housing 105 includes a solenoid magnet and bore area 101, where a human patient may be placed to be scanned. The solenoid magnet may be generally known as the main magnet. The solenoid magnet may generate a substantially uniform magnetic field for imaging the human patient placed inside bore area 101. This magnetic field may generally serve as a static polarizing field.

Figure 1B:
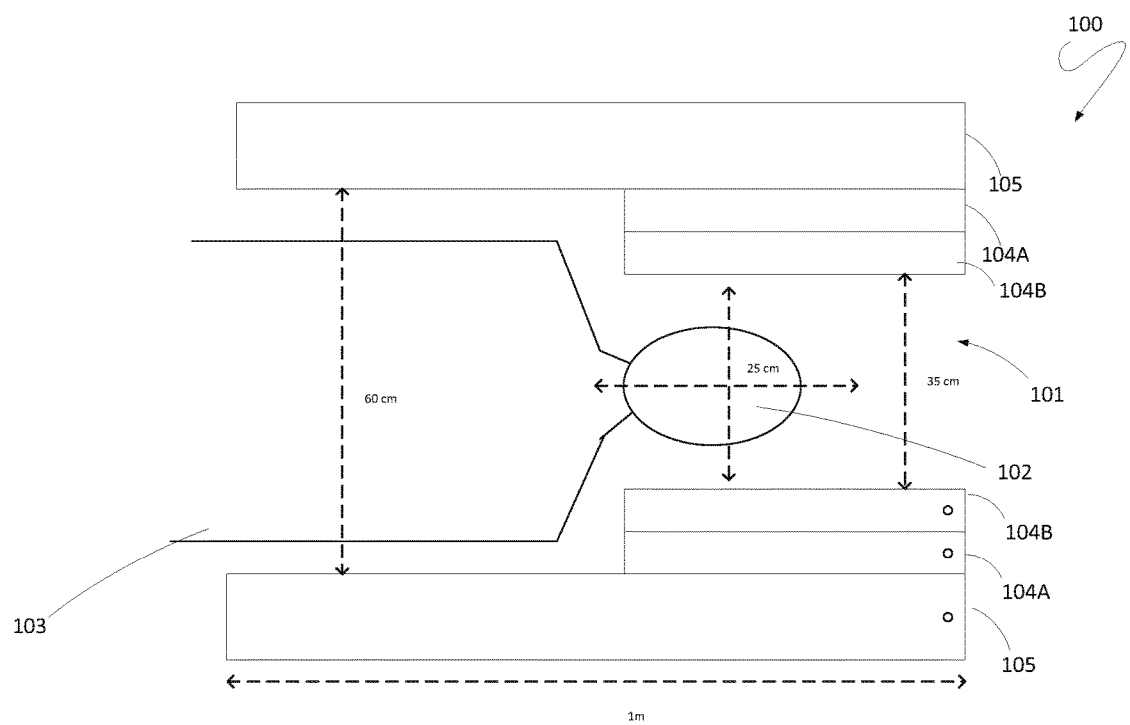
FIG. 1B shows a profile view of the MRI system configured for safe shutdown.

Referring to FIG. 1B, patient 103 can be placed in bore area 101. In this example, patient head area 102 is placed inside the magnetic field to be imaged by coil assembly 104. As shown in FIGS. 1A and 1B, coil assembly 104 is shaped as an annular structure and housed within the inner bore of solenoid magnet. In this example, coil assembly 104 includes a gradient coil 104A and an RF coil 104B. The gradient coil 104A may generate a perturbation of the static polarizing field to encode magnetizations within the human patient's body. In some configurations, coil assembly 104 may include a radio frequency (RF) coil 104B to transmit RF pulses as excitation pulses. The RF coil 104B may also be configured to receive MR signals from the human patient in response to the RF pulses. In some instances, housing 105 may include separate receive coils to receive the MR signals from the human patient. In these instances, radio-frequency (RF) signals are, for example, received by local coils for imaging a subject. In one example, a head coil in a birdcage configuration is used for both transmitting and receiving RF signals for imaging the subject's head area 102. In another instance, RF coil 104B is used for transmitting an RF signal into the subject and a phased array coil configuration is used for receiving MR signals in response.

Figure 2:
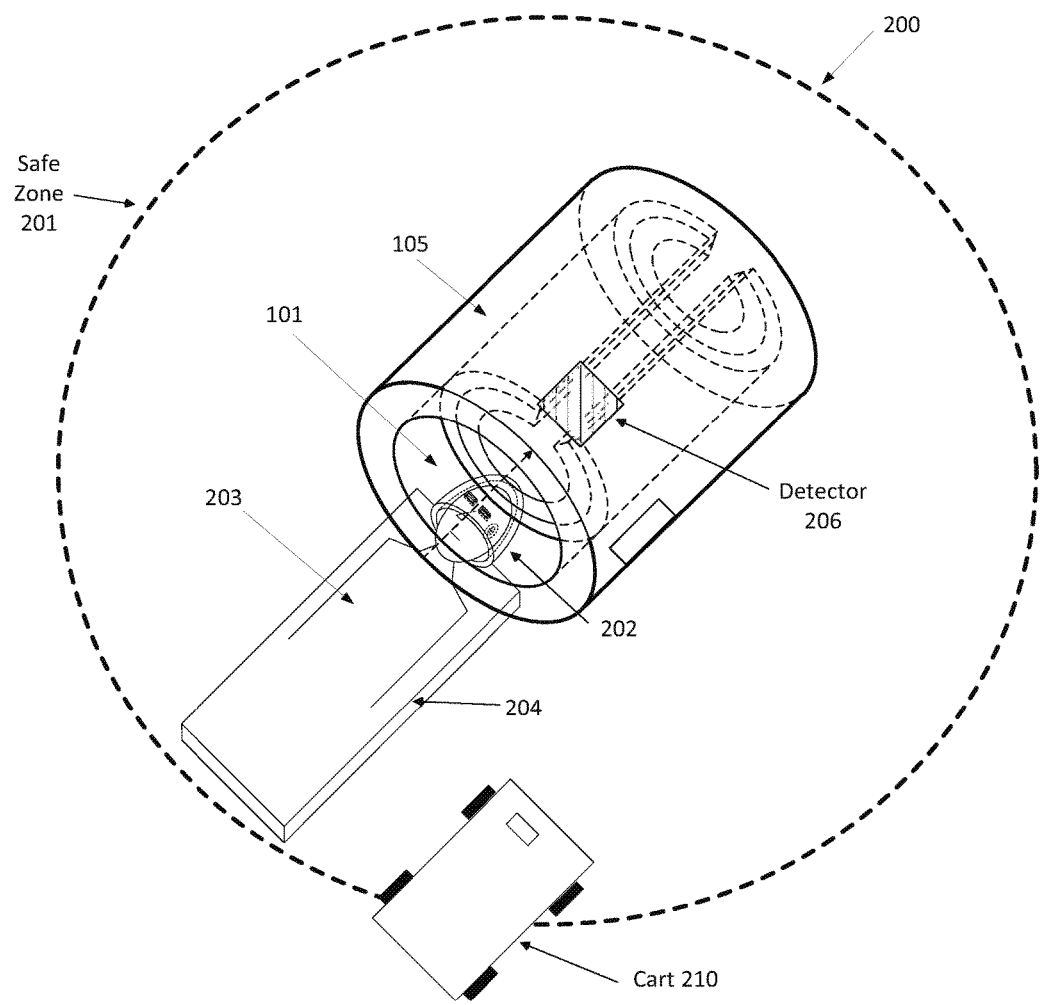
FIG. 2 illustrates an example of an MRI systems configured for safe shutdown.

Referring now to FIG. 2, a safety zone 201 may be prescribed inside scanning room 200. Safety zone 201 may represent a region in which the presence of suspected MR-incompatible objects would trigger a safe shutdown of the magnet. In some instances, safety zone 201 extends outside the fringe field (defined by, e.g., the 5 Gauss line) of the magnet. In other instances, safety zone 201 may cover the same area as the fringe field (defined by, e.g., the 5 Gauss line) of the magnet. In still other instances, safety zone 201 may cover an area within the 5-Gauss line perimeter, for example, a 10-Gauss line. As disclosed herein, MR-incompatible objects refer to objects that pose an operational hazard to the MRI system. Examples include ferromagnetic objects such as ferromagnetic objects. Magnet housing 105 includes solenoid magnet and bore area 101, where a human patient 203 may be placed to have an MRI of his or her head region 202. In this illustration, human patient 203 is placed on patient bed 204 that is slide-able into bore area 101. In this example, cart 210 is located inside safety zone 201. The cart 210 may be brought into the scanning room when patient 203 was transported in. The cart 210 may include MR-incompatible objects, for example, oxygen tanks (including metal cover) and mechanical tools (such as wrenches).

Such objects may pose an operational hazard because these objects are typically magnetic and can become projectiles flying into magnet housing 105, damaging the magnet or even patient 203 who may be undergoing an MRI procedure in bore 101. Some implementations incorporate a detection system 206 including, for example, a control unit and one or more sensor devices. The one or more sensor devices are configured to determine location information that indicates the location of such an object relative to MRI system 100. Based on this information, the control unit can determine if the object poses an operational hazard, for example, because it is inside safety zone 201. If the control unit determines the object poses an operational hazard, the control unit may take action, such as causing a reduction of the field strength of the magnet. In some instances, one or more airbags (as an example of a physical barrier) may be inflated to buffer the potential impact from a possible projectile.

The detection system may employ one or more detection mechanisms to identify the operational hazard in the scan room. As explained below, examples of the detection mechanism include an optical approach, a radio-frequency (RF) approach, a magnetic approach, or an inductive approach. The optical approach may employ sensor devices such as one or more camera devices or even infrared (IR) sensors. The RF approach may utilize sensor devices that include antenna devices for transmitting and receiving RF waves. The magnetic approach may employ sensor devices that leverage the use of magnetic field probes while the inductive approach may employ a sensor device that senses the inductive effect on the current powering the magnet caused by magnetic objects in the field of the magnet.

As noted above, in some instances, the detection system 206 may include a camera device. The camera device may operate in visible light or infrared ranges. In one example, the camera device may be mounted on the magnetic housing 105. In another embodiment, the camera device may be located outside the room, for example, in the console room, to monitor the scan room through a glass shield. As an illustration, the camera device can capture video frames and then process the captured video frames to identify potentially MR-incompatible objects and track the motions of the identified objects. Examples of such objects include anesthesia carts, oxygen tanks, or working tools such as wrenches. The readout from the camera device, for example, a live video feed, may serve as one source of input data for further processing by the detection system 206, as discussed further below.

In some cases, the detection system 206 may include a system that leverages the readout from optical or electromagnetic (EM) tracking markers placed on potentially MR-incompatible objects. Examples of optical tracking markers include fluorescent objects, or light-emitting-diodes. For illustration, the system may monitor the positional information of such objects in the scan room by sensing the whereabouts of optical or EM tracking markers and projecting the positional information on a live video stream of the scan room. Generally, the sensed positional information can be another source of input data for further processing by the detection system 206, as discussed further below.

In some instances, the detection system 206 may include a laser projector device to emit, for example, infrared (IR) beams. In one illustrative example, the laser projection device rotates a transmitting IR beam to scan the surroundings. In these instances, photosensors (such as photodiodes) may be placed around the perimeter inside the scan room to detect any blockage of projected laser beam from laser projector 206. For example, laser sensors may be placed on the floor along the perimeter of the safety zone 201, or along the shoe molding level of the sidewalls of the scan room. Some implementations of laser projector may further include photosensors (such as photodiode devices) to receive laser reflections due to blocking objects. The readout may be communicated to a control unit of MRI system 100, which controls the power supply of the magnet. Such readout may generally serve as yet another source of input data for further processing by the detection system 206, as discussed further below.

The detection system 206 may also operate in radio frequency (RF) ranges. In one example, a sensor device may include a transmitting RF antenna to rotate a RF beam around the scan room, searching for potentially MRI-incompatible objects in a manner similar to the laser projector device described above. In this example, a receiving RF antenna may be placed on the floor around the perimeter of safety zone 201, or around the shoe molding level of the surrounding walls to detect blockage any RF beams. The transmitting RF antenna of the sensor device mounted on top of magnet housing 105 may operate in duplex mode to receive RF beams reflected from objects in the scan room. Such monitoring approaches can be extended to monitoring using ultrasound beams. The monitored range information can be still another source of input data for further processing by the detection system 206, as discussed further below.

Some implementations may place a sensor device on MRI-incompatible objects in the scan room. For example, such a sensor device may be placed on an anesthesia cart and configured to detect and transmit location data indicating a location of the cart. In some instances, the location data may include proximity data indicating the distance between the sensor device on the object and sensor device mounted on magnet housing 105. Such location data may be communicated to the control unit of detection system 206. The communication between sensor devices and the control unit may be through a wireless technology such as BlueTooth, infrared, WiFi, cellular, etc. In other instances, the location data may also indicate a motion or acceleration of cart 210 in the scan room. When acceleration motion is detected, one or more air bags may be inflated to buffer the potential impact of the accelerating object hitting magnet housing 105 or patient 103 inside bore 101. The EM operating frequency may be chosen to avoid aliasing with respect to the Larmor frequency, at which the MRI system 100 operates to generate an MR image of patient 103. Such location data broadcast from sensor devices may be yet still another source of input data for further processing by the detection system 206, as discussed further below.

Some configurations may leverage a magnetic readout. For example, sensor devices may be magnetic field probes placed on objects which can pose an operational hazard within safety zone 201 (e.g. an anesthesia cart). If the magnetic field probe detects that it is within a magnetic field above a certain threshold, the field probe may send a signal, for example, via radio wave or infrared light. Example magnetic field probes include Gauss meters or Hall probes. The readout signal may be communicated to a control until, which may then analyze and compare the readout value to a numerical threshold. If the readout value is indeed over the threshold safety value, a shutdown signal may be directed to the power supply of the MRI system to trigger a shutdown of the magnet. The magnetic readout may also serve as an additional source of input data for further processing by detection system 206, as discussed further below.

Some implementations may exploit the inductive effect caused by a magnetic object that moves quickly through the magnetic field of the magnet. Specifically, such motions can induce fluctuations in the current of superconducting wires powering the magnet. The effect is due to inductive coupling between the object and the magnet of the MRI system 100. A sensor device may measure the level of current fluctuation, which can then be compared to a threshold. If the fluctuation is above the threshold level, the control unit of detection system 206 can trigger a shutdown sequence to turn down the power supply of the magnet. The readout from this inductive approach may be an additional source of input data for further processing by detection system 206, as discussed further below.

The readouts from one or more of these various mechanisms may be consolidated at the control unit of detection system 206 to render a determination as to the nature of the object as well as the level of threat. In instances where more than one type of mechanism is used, the various readings may be used to corroborate each other to enhance the confidence that a detected object poses a threat. For example, a readout from a camera device may detect the presence of an object in the scan room, while a readout from a magnetic field probe placed on the object may confirm that the detected object is seeing a magnetic field above a threshold level. Once a final determination is made based on the combined readout that the detected object poses an operational hazard, precautionary steps may be taken by the control unit to turn down the magnet, including releasing an airbag to protect patient 103 being scanned in bore area 101 and/or reducing the magnetic field of the magnet. In one illustrative example, a sensor device, such as a force device or an accelerometer, may be mounted on magnet housing 105 to detect the impact of an object hitting magnet housing 105. If an impact is being detected and a human patient is being scanned in bore 101, one or more air bag may be released to protect the patient.

In some implementations, turning down the magnet may not cause a controlled quench of the magnet. Instead, in these implementations, the magnetic field of the magnet can be ramped up after the detected hazard is gone. For example, once the hazard is detected, the control unit of MRI system may initiate automatic field reduction while signaling human intervention. When it is determined that the operational hazard is removed, for example, when cart 210 is removed from scan room by a human operator, a control unit of MRI system may initiate automatic ramping up to bring the magnet back to normal operation ready for scanning patients.

For context, the wires that carry current are typically in a superconducting state to power, for example, the solenoid magnet of the MRI system. In this superconducting state, the wires can carry large amounts of current for generating a strong magnetic field of, for example, 1 Telsa or above. Maintaining this superconducting state generally means that the wires are kept at a cryogenic temperature (e.g., below a certain critical temperature). As an illustration, temperature of the solenoid magnet is normally at 4 Kelvin. Typically a helium compressor is used for maintaining the low temperature for the wires. If the helium compressor loses its alternate current (AC) main power (or the helium compressor is disconnected, or a cable damaged, etc.), the solenoid magnet will gradually warm up until the critical temperature of the superconducting wire is reached, at which point the wire would become resistive, and the resistive losses in the wire would cause a sudden increase of magnet temperature (also known as a quench) due to resistive heating and subsequently a precipitous drop in the amount of current carried by the wires. In this event, the magnet temperature rapidly rises to a much higher temperature such as 50 Kelvin. The MRI system will be inoperable until the magnet temperature is lowered back to, for example, 4K, which could take several hours or even longer. To avoid this undesirable delay, the magnet temperature can be monitored. If a loss of cooling is detected, the MRI system can initiate a ramp down of the magnet. If the magnet has been ramped down (e.g., no current in the magnet wires) when the temperature crosses the superconducting critical temperature threshold, then there would be no quench, and no rapid increase in temperature. By adding this feature, the time for the magnet to be ramped up back for operation can be reduced.

Figure 3:
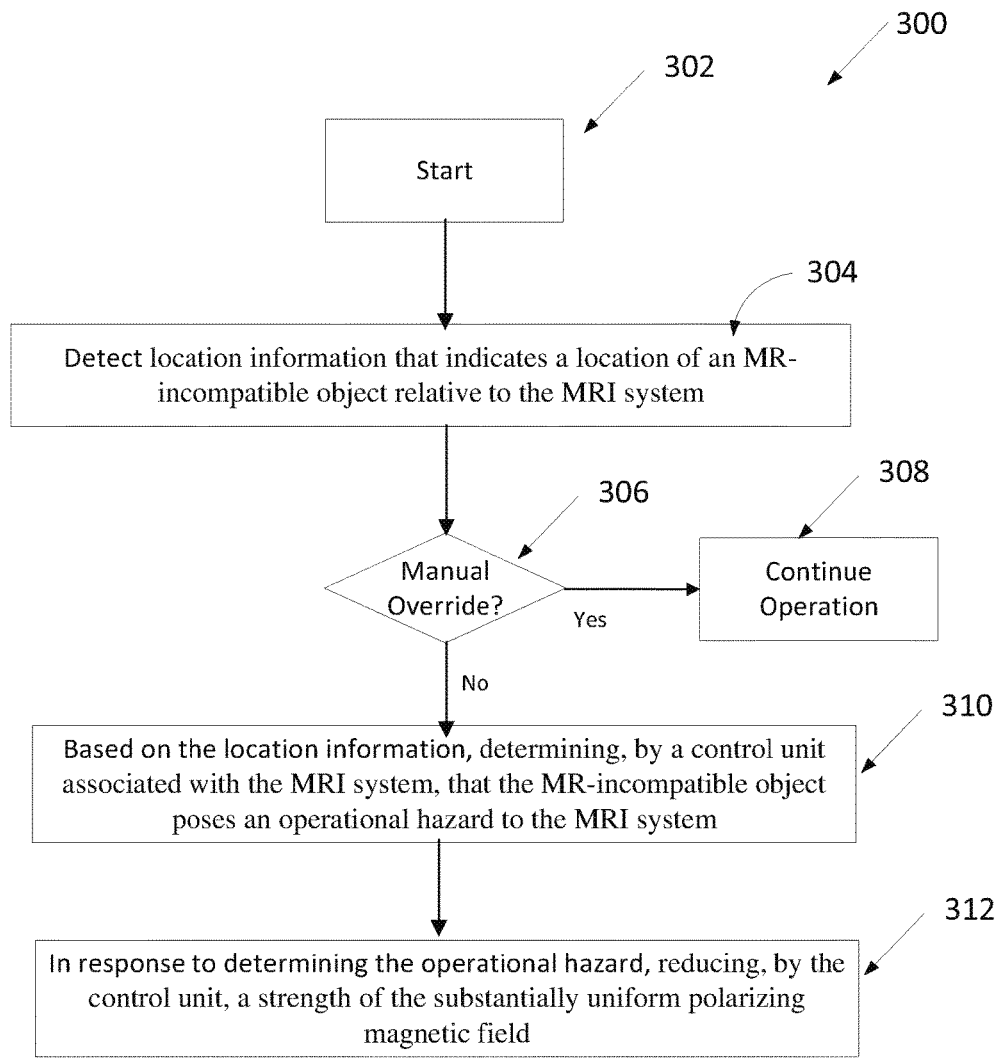
FIG. 3 is a flow chart showing an example of a process for automatic safe shutdown of a magnet of an MRI system.

FIG. 3 is a flow-chart 300 summarizing a process for safe shutdown of a magnet. After the process starts (302), a sensor device determines location information that indicates a location of an MR-incompatible object relative to the MRI system (304). Such determination may leverage a camera device configured to monitor the scan room for MR-incompatible objects. In the example of a camera device, the location information determination may incorporate image processing of video frames captured by the camera device. As discussed herein, the MRI system generates a substantially uniform polarizing magnetic field for imaging a subject. Next, the process determines whether there is manual override (306). Manual override means a human operator is taking over the operation of MRI system 100. If there is manual override, the MRI system 100 continues operation under the guidance of the human operator (308). If there is no manual override, then based on the determined location information, a control unit associated with the MRI system determines whether the MR-incompatible object poses an operational hazard to the MRI system (310). The operational hazard determination may include determining whether the MR-incompatible object is present within a safety zone of a main magnet of the MRI system. The operational hazard determination may be based on consolidated input from more than one sensor devices, not merely the camera device. In one instance, the operational hazard determination may include a determination of whether the object is accelerating towards the main magnet. In response to determining that the MR-incompatible object poses an operational hazard to the MRI system, the control unit may cause air bags to be inflated or a reduction of a strength of the substantially uniform polarizing magnetic field (312). This reduction may include the initiation of a shutdown sequence for the magnet. When the operational hazard is no longer a threat, for example, when cart 210 has been removed from scan room, the control unit may cause a ramp-up of the strength of the substantially uniform polarizing magnetic field and normal operations of the MRI system may resume.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is claimed is:

1. A magnetic resonance imaging (MRI) system, comprising:
    a housing having a bore in which a subject to be imaged is placed;
    a main magnet accommodated by said housing and configured to generate a polarizing magnet field with the bore;
    pulse generating coils configured to generate and apply radio frequency (RF) pulses in sequence to scan the subject;
    gradient coils configured to provide perturbations to the polarizing magnet field that encode MRI signals acquired in response to the applied RF pulses; and
    a control unit coupled to the main magnet and configured to:
    access location information that indicates a location of an MR-incompatible object relative to the MRI system;
    based on the location information, determine whether the MR-incompatible object poses an operational hazard to the MRI system; and
    in response to determining that the MR-incompatible object poses an operational hazard to the MRI system, reduce a strength of the polarizing magnetic field.

2. The MRI system of claim 1, wherein the polarizing magnetic field is substantially uniform.

3. The MRI system of claim 1, wherein the control unit is configured to receive location information of the MR-incompatible object from a sensor mounted on the MR-incompatible object.

4. The MRI system of claim 3, wherein the sensor comprises one of: a Gauss meter, a Hall probe, a magnetic field probe, or an optical tracker.

5. The MRI system of claim 1 further comprising a camera, wherein the control unit is configured to process images from the camera to determine the location information of the MR-incompatible object.

6. The MRI system of claim 1 further comprising a current sensor, wherein the control unit is configured to process a signal from the current sensor to detect a change in a current that powers the main magnet, the change being induced by a motion of the MR-incompatible object within the polarizing magnetic field.

7. The MRI system of claim 1, wherein, to reduce the strength of the polarizing magnetic field, the control unit is configured to initiate a shutdown of the main magnet.

* * * * *